US006132416A

United States Patent [19]
Broselow

[11] Patent Number: 6,132,416
[45] Date of Patent: Oct. 17, 2000

[54] UNIVERSAL MEDICATION DOSING SYSTEM

[76] Inventor: James B. Broselow, 1315 Wessex La., Hickory, N.C. 28602

[21] Appl. No.: 09/145,009

[22] Filed: Sep. 1, 1998

[51] Int. Cl.[7] .................... A61M 31/00
[52] U.S. Cl. .................... 604/506; 128/898
[58] Field of Search .................... 604/500, 50 B, 604/189; 128/898

[56] References Cited

U.S. PATENT DOCUMENTS

| | | | |
|---|---|---|---|
| 4,713,888 | 12/1987 | Broselow . | |
| 4,823,469 | 4/1989 | Broselow . | |
| 4,926,885 | 5/1990 | Hinkle . | |
| 5,010,656 | 4/1991 | Broselow . | |
| 5,016,651 | 5/1991 | Stalcup et al. | 128/898 |
| 5,468,224 | 11/1995 | Souryal | 604/51 |
| 5,573,529 | 11/1996 | Haak et al. | 606/1 |
| 5,773,258 | 3/1998 | Lane | 604/51 |

OTHER PUBLICATIONS

Critical Care Medicine; "A pediatric gastric tube airway" by The Williams & Watkins Co.; vol. 9, No. 5, pp. 426–427; 1981.

*Primary Examiner*—Wynn Wood Coggins
*Assistant Examiner*—Deborah Blyveis
*Attorney, Agent, or Firm*—Adams, Schwartz & Evans, P.A.

[57] ABSTRACT

A method of determining the proper medication dosage for a patient, including the steps of correlating a plurality of dosages of a plurality of medications to respective weight-related values indicative of the proper dosage of each of the medications for a given patient weight range, assigning a color to each of the respective weight-related values within a predetermined, fixed sequence of colors collectively representing a dosage range for each of the medications, wherein each of the colors represents a proper dosage for each medication for a patient having a weight within the weight range to which the color is assigned, and providing a dosing system which correlates each of the dosages of the medications with the assigned color within the fixed sequence of colors without regard to the potency of said medication.

11 Claims, 4 Drawing Sheets

Intravenous Medications

Single Dose Antibiotic Powder
for reconstitution and oral use

OTC Oral medications

UNIVERSAL MEDICATION DOSING SYSTEM

TECHNICAL FIELD AND BACKGROUND OF THE INVENTION

This invention relates to a universal medication dosing system designed to aid in the practice of pediatric medicine. Medication dosing is simplified by the development of color-coded dosing zones based on patient weight or length, depending on the circumstances. When weights are readily available, such as in offices, clinics, or hospitals, weight is used as the universal dosing value. When weight is not available, the child's length can be used to determine his "color." Once the proper dosing "color" has been established, the color remains the same for all medication dosing so long as the child's weight or length remain with the range of weights or lengths applicable to that color.

Length-based dosing will often be more appropriate for emergencies where weight is frequently not known. This system can also be used for home dosing of medications where accurate weights are also usually not available. All patients within a given zone would be given the same dose range of medication.

The invention also has application for determination of other physical treatment values, such as the proper size of pediatric equipment, ventilator settings, infusion devices, etc. The zones would be labeled with the name of the color for use by those who are color blind.

In adult medicine the dosing of medications and selection of appropriately-sized equipment is straightforward. A cardiac arrest, for instance, can be treated by giving "an amp" of epinephrine or bicarbonate. Likewise the initial dose of atropine for an adult may be given as 0.5 mgs of atropine for bradycardia. This dosage may be given safely to a broad spectrum of patients. Similarly an adult with a fever can take two aspirins or two Tylenol tablets and feel comfortable that he has taken an appropriate dose. An adult patient can be intubated with one of only a few sizes of endotracheal tubes, and it is not difficult to learn which size tube to use based on experience in dealing with differently-sized adults. This is obviously not the case in pediatrics. Children's sizes vary tremendously from the smallest premature infant to a large pre-pubital child. There are more than ten endotracheal sizes that may be appropriate for different size pediatric patients. Medications are most commonly dosed according to patient weight and dosages are expressed in ranges of mgs/kg. To arrive at an appropriate dose one must know the patient's weight, the formula in mg./kg., and the concentrations of the drug which are available. Then, mathematical calculations must be done to arrive at the appropriate dosage. Using weight to dose becomes problematic in circumstances where weight is not known. This is true in emergency situations such as pediatric cardiac arrests, seizures, and trauma situations. In addition, it is quite difficult to remember formulas and do mathematical computations accurately in the excitement of a pediatric resuscitation. It may take even a seasoned clinician years to get used to the nuances of dosages and equipment sizes and equipment settings in children. Even with experience, few clinicians are really comfortable with giving children drugs such as IV sedatives, pain medications, paralyzing agents, to name only a few.

The everyday practice of pediatrics is constantly interrupted by the question of how much of a given drug should be given to a particular pediatric patient. Physicians such as orthopedists and surgeons spend a significant amount of time looking up dosages. Frequently sufficient time is not taken, or inadvertent mistakes are made, or the dosages are determined by educated guess, giving erratic and inconsistent dosages of many medications to children. In emergencies this problem is magnified because there may not be time to look up the dosage.

This also creates problems for nurses who are responsible for giving the proper dosage, yet may not have the time to verify an order under these circumstances. In addition, non-physicians may be called upon to dose children under emergency situations such as a paramedic treating a child who is seizing with IV or rectal Valium, or cardiac arrest. Even an emergency physician may feel uncomfortable with IV demerol for a child with a broken leg, in part due to concern about giving the proper dose to give pain relief without developing respiratory insufficiency. The resulting dilemma tends to lead to underutilization of pain medications and undue suffering to the pediatric patient.

This problem also impacts the field of medical education where each year there is an influx of first year residents who are called upon to dose children in hospitals and clinics. Unfortunately, even the best of childrens' hospitals and medical centers report their share of dosing mistakes, occasionally with tragic outcomes. This problem is not unique to the medical community. The lay public has great concerns about giving medications to children. Studies have shown that in the common scenario of a child with a fever, dosages of acetaminophen are frequently inadequate and ineffective, contributing to marked parental anxiety. Inadequate dosing may also contribute to unnecessary trips to emergency departments, since a fever that doesn't come down with antipyretics is a common reason for an ED visit. Deaths have been reported resulting from inadvertent overdosing of fever medication at home. Even physicians are concerned about how much of such seemingly innocuous agents as decongestants and cold preparations to give their own children or grandchildren. If they don't practice pediatrics, they may find themselves calling a colleague to ask how much Dimetapp to give their one year old child.

In addition, the FDA has been hesitant to give dosing information to the public for young children. The bottle label tells them to call their doctor for instructions. This is not, however, a practical solution to this problem since they may not have a doctor or he may be unavailable at that time. In addition, many people do not feel comfortable calling under those circumstances, and find themselves giving medication anyway, perhaps asking a grandmother how much, or just taking a guess at the amount.

This entire problem is compounded by the large number of people who are both professionally and personally called upon to give medications to children. At the top are pediatricians who are quite adept at dosing pediatric patients, except possibly in the area of pediatric emergencies. However, many other medical specialties are called upon to dose children and lack the expertise of pediatricians. At best it can be very time-consuming for physicians and nurses to find the proper dose. At worse, mistakes are made. In addition there are paramedics, nurse practitioners, physician's assistants, health department nurses, daycare center personnel, teachers and parents, all whom may be called upon to decide how much medication a child should take.

In the area of pediatric emergency medicine this problem has been previously addressed by the development of a tape measure, the Broselow Tape, which allows the dosage of medications and equipment sizes to be determined from a direct length measurement of the patient. The tape is disclosed in U.S. Pat. No. 4,713,888. This has been found to be useful since it makes unnecessary the estimation of weight in an emergency, memorization of infrequently used formulas and the necessity to do mathematical calculations under duress. The equipment zones on the Broselow tape are color-coded to allow storage and access of emergency equipment by color, allowing more rapid access and easier restocking. For these reasons, the Broselow tape is now well accepted and widely used.

This application relates to the development of a universal pediatric dosing system based on the concept of developing dosing zones not only for equipment but for drugs as well. These zones would be designed so that all children within the zone could be given the same dosage instructions specific for that drug. The dose could be a single fixed amount such as for liquid Tylenol, or could be a range for titrating IV medications such as demerol or Versed. For example, assume that a child presents to an emergency department with a painful fracture. His color could be obtained from a Broselow tape while lying on the stretcher. If he were in the "blue" zone, he would be given the "blue dose" of demerol. The "blue dose might say "give 10 mgs of Demerol IV every 3 to 5 minutes until pain relieved." If the child were to become unduly sedated, he could be given the "blue dose" of Narcan. It seems likely that a child would more readily be given pain medications if dosing were not an issue.

A similar example could be given for a child who needs sedation for a CT scan. It would be a simple matter for the radiologist to order an appropriate dose without having to confer with the hospital pharmacy or a pediatrician. Surgery procedures could also be indexed by the dosing color. For instance, the procedures could be identified as "three blue cases and two red cases this morning in surgery."

This would allow the drugs and equipment for each case to be prepared prior to surgery. The pre-op medications and pain medications as well as anesthetics would all be indexed to this color. The maintenance fluids during surgery could be given by setting the infuser to the proper color. The simplest way the system could be implemented would be the addition of a colored dosage page to each chart. On that page would be written commonly used pediatric drugs in the proper dose for a patient of that dosage color. It could be used as a single reference for all the health care providers dealing with that patient. It would have both elective and emergency drugs calculated for that patient. It could also incorporate maximal doses of potentially toxic drugs and thus used as a "failsafe" mechanism for those drugs. The color could also be incorporated into the actual dosing vehicle such as color-coded syringes. These syringes can be particularly useful in the area of pre-hospital treatment of pediatric emergencies. Likewise, the colors could be incorporated into dosing devices for the public such as color-coded cups, syringes, etc. for use with OTC medications. The system would always be available to the clinician if he desired to use it. However, it could be overridden at all times. If the physician did decide to use other methods to arrive at dosages, the color-code would still allow the nurse administering the drug to quickly check a reference before giving the medication if she were unsure of the proper dosage for that patient. In other words it could function as a "failsafe" mechanism for dosing children.

For instance, the pharmacy of the hospital could put a "rainbow label" on each medication. It would consist of the name of the medication, the concentration and the eight dosing colors. Within each color would be written the dose in the appropriate number of cc's. At the beside the nurse would check the patient's arm band to determine his color and then check the rainbow label of the medication to make sure that the dosage ordered was appropriate. If she had brought another patient's medication by mistake, she would probably be warned there night be an error since the dose would typically be incorrect. In the pre-hospital arena the color would function like a "vital sign." A first responder could call the color of a sick or injured child into central dispatch. The color would help the system anticipate the child's drug, fluid and equipment needs. In addition, it would help the system prepare for the probable etiologies of the problem. For instance acute respiratory distress in a "blue" would have different probable causes than in a "pink." One further advantage of the color-coded dosing system is that it can become the vehicle for disseminating EMS-C and Safe Kids concepts into the daily practice of medicine. The simplicity of the system should encourage both the public and professionals to turn to color-coded sources for dosing information. Injury and accident instructions as well as aftercare instructions could all be related to the child's "color." It would help people focus on the different needs of children of different sizes in a simple and visually graphic way. By incorporating injury and accident prevention information into these materials, they would serve as an important reminder to health care professionals to reinforce these important messages with each patient encounter. When one looks at the tremendous variety of situations in which children are given medications, color coding is an effective way of enhancing reliability, safety and efficacy.

SUMMARY OF THE INVENTION

Therefore, it is an object of the invention to provide a drug dosing system which reduces the possibility of incorrect dosing.

It is another object of the invention to provide a drug dosing system which does not require reformulation of existing drug concentrations or potency.

It is another object of the invention to provide a drug dosing system which is color-coded so as to be usable by individuals who do not read, or who cannot read a particular language in which dosing instructions would ordinarily be given.

It is another object of the invention to provide a drug dosing system which insures by code, packaging or some type of physical mating or dispensing device that the appropriate amount of drug is dispensed for a given color-correlated drug concentration or potency.

It is another object of the invention to provide a drug dosing system which correlates weight-related values indicative of a proper dosage with a predetermined, arbitrary color.

These and other objects of the present invention are achieved in the preferred embodiments disclosed below by providing a method of determining the proper medication dosage for a patient, comprising the steps of correlating a plurality of dosages of a plurality of medications to respective weight-related values indicative of the proper dosage of each of the medications for a given patient weight range, assigning a color to each of the respective weight-related values within a predetermined, fixed sequence of colors collectively representing a dosage range for each of the medications, wherein each of the colors represents a proper dosage for each medication for a patient having a weight within the weight range to which the color is assigned, and providing a dosing system which correlates each of the dosages of the medications with the assigned color within the fixed sequence of colors without regard to the potency of the medication.

According to another preferred embodiment of the invention, the method includes the step of prescribing a medication dosage of any of the plurality of medications by assigning a single color within the fixed sequence of colors to a patient based on the weight range of the patient which provides a proper dosage amount for each of the plurality of medications.

According to another preferred embodiment of the invention, the method includes the steps of providing a medication container for a liquid medication having a medication-dispensing orifice with a predetermined-shape unique to the type and strength of the medication. A dosing syringe is provided having a elongate medication-receiving barrel for dispensing medication from the medication container. The barrel has a size and shape adapted for being matingly-received in the medication container orifice for dispensing medication from the medication container. A dosage of the medication is determined by assigning a single color to a patient based on the weight range of the patient which provides a proper dosage amount for each of the plurality of medications.

According to yet another preferred embodiment of the invention, the method comprises the steps of correlating a plurality of dosages to respective weight-related values indicative of the proper dosage of the medications for a given patient weight range. A color is assigned to each of the respective weight-related values within a predetermined, fixed sequence of colors collectively representing a dosage range for the medication. Each of the colors represents a proper dosage for the medication for a patient having a weight within the weight range to which the color is assigned.

According to yet another preferred embodiment of the invention, the method includes the step of prescribing a medication dosage by assigning a single color within the fixed sequence of colors to a patient based on the weight range of the patient which provides a proper dosage amount for each of the plurality of medications.

According to yet another preferred embodiment of the invention, the method includes the steps of providing a medication container for a liquid medication having a medication-dispensing orifice with a predetermined-shape unique to the type and strength of the medication. A dosing syringe having a elongate medication-receiving barrel is provided for dispensing medication from the medication container. The barrel has a size and shape adapted for being matingly-received in the medication container orifice for dispensing medication from the medication container. A dosage of the medication is prescribed by assigning a single color to a patient based on the weight range of the patient which provides a proper dosage amount for the medication.

A method of determining the proper medication dosage for a patient according to another embodiment of the invention comprises the steps of correlating a plurality of dosages of a medication to respective values indicative of the proper dosage of each of the medications for a given patient, wherein the values represent a direct correlation between the heel-to-crown height of a patient and the dosage. A color is assigned to each of the respective values within a predetermined, fixed sequence of colors collectively representing a dosage range for the medication, wherein each of the colors represents a proper dosage for the medication for a patient having a weight within the weight range to which the color is assigned.

Yet another method of dosing a patient includes the step of prescribing a medication dosage of the medication by assigning a single color within the fixed sequence of colors to a patient based on the weight range of the patient which provides a proper dosage amount for the medication.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
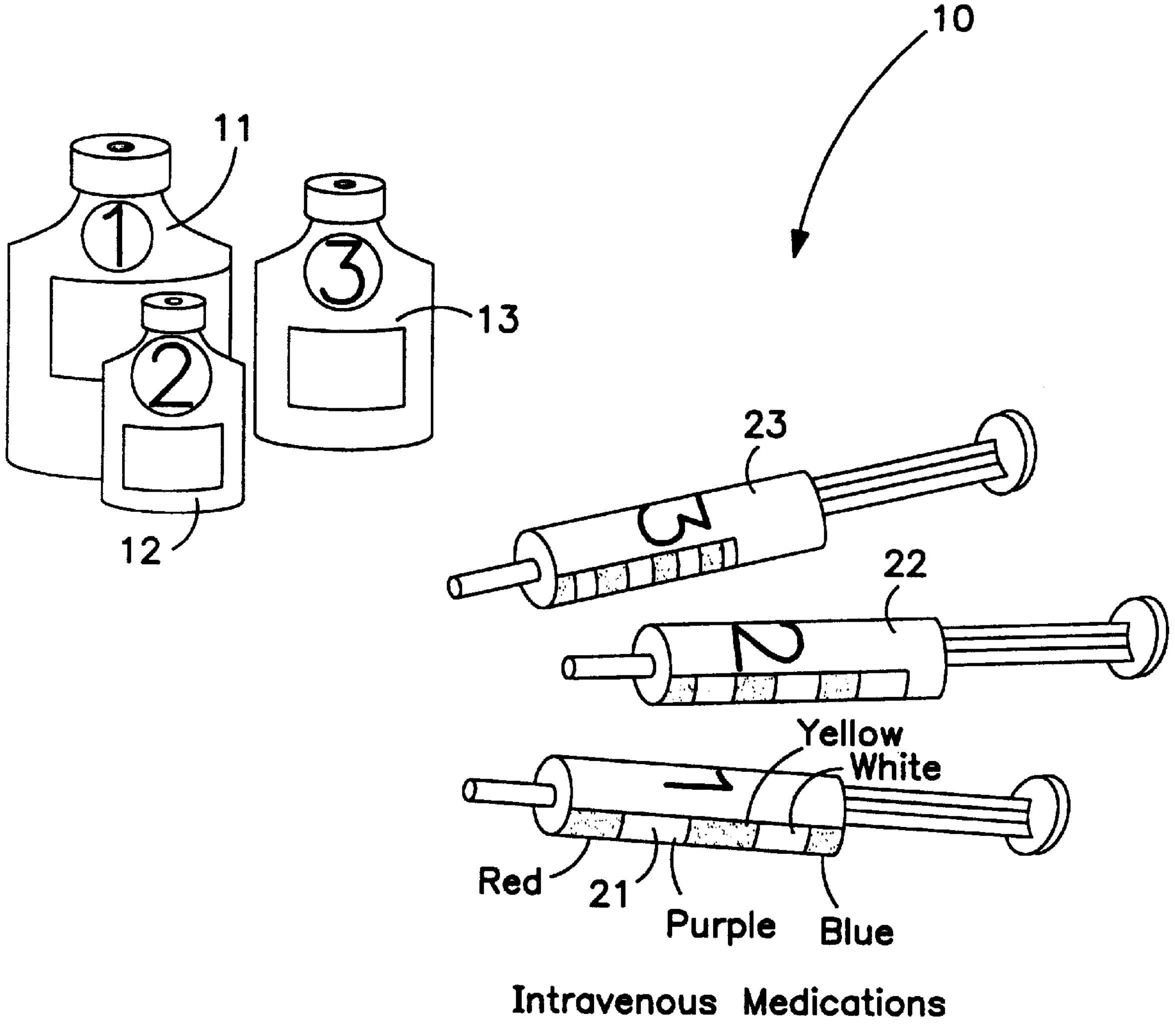
FIG. 1 is an illustration of a dosing system for intravenous medications which uses a mating syringe and dispensing bottle.

Referring now specifically to the drawings, a dosing system according to an embodiment of the invention is shown in FIG. 1 at reference numeral 10. The system 10 includes dispensing containers, for example, bottles 11, 12 and 13, numbered “1”, “2” and “3”, respectively. Complementary dosing syringes 21, 22 and 23 cooperate with the bottles 11, 12 and 13 to insure proper dosing.

Bottles 11, 12 and 13 represent drugs of different concentrations. These concentrations are conventional, and a major advantage of the invention is that the multitude of existing drugs need not be reformulated. Rather, drugs are grouped according to concentration. A correlation such as disclosed in the Broselow U.S. Pat. No. 4,713,888 is used, and a given color is selected so that, for example, a dosage for a patient of a given weight or body length is always, for example, blue. As shown in FIG. 1, intravenous medications are dispensed by matching a syringe 21 with the number “1” on it is used only to dispense from bottle 11 with a “1” on it. Likewise, syringe 22 is used to dispense only from a bottle 12 with a “2” on it, and a syringe 23 is used to dispense only from a bottle 13 with a “3” on it.

As is also shown in FIG. 1, each of the syringes 21, 22 and 23 are marked with colored gradations representing incremental dosages. In each case, the same order of colors are used to represent different dosages, for example, red, purple, yellow, white and blue. If, hypothetically, a nurse was instructed to inject a pediatric patient with three drugs represented by bottles 11, 12 and 13, three syringes 21, 22 and 23 would be used, and in each case the prescribed amount of the drug would be represented by a single color. So, for example, if the child based on his weight or length was a “yellow”, the nurse would syphon the drug from the bottle up to the “yellow” mark on the syringe. In short, all the nurse has to know is that the patient is a “yellow”, and dosing becomes easy and reliable, even under difficult conditions.

Figure 2:
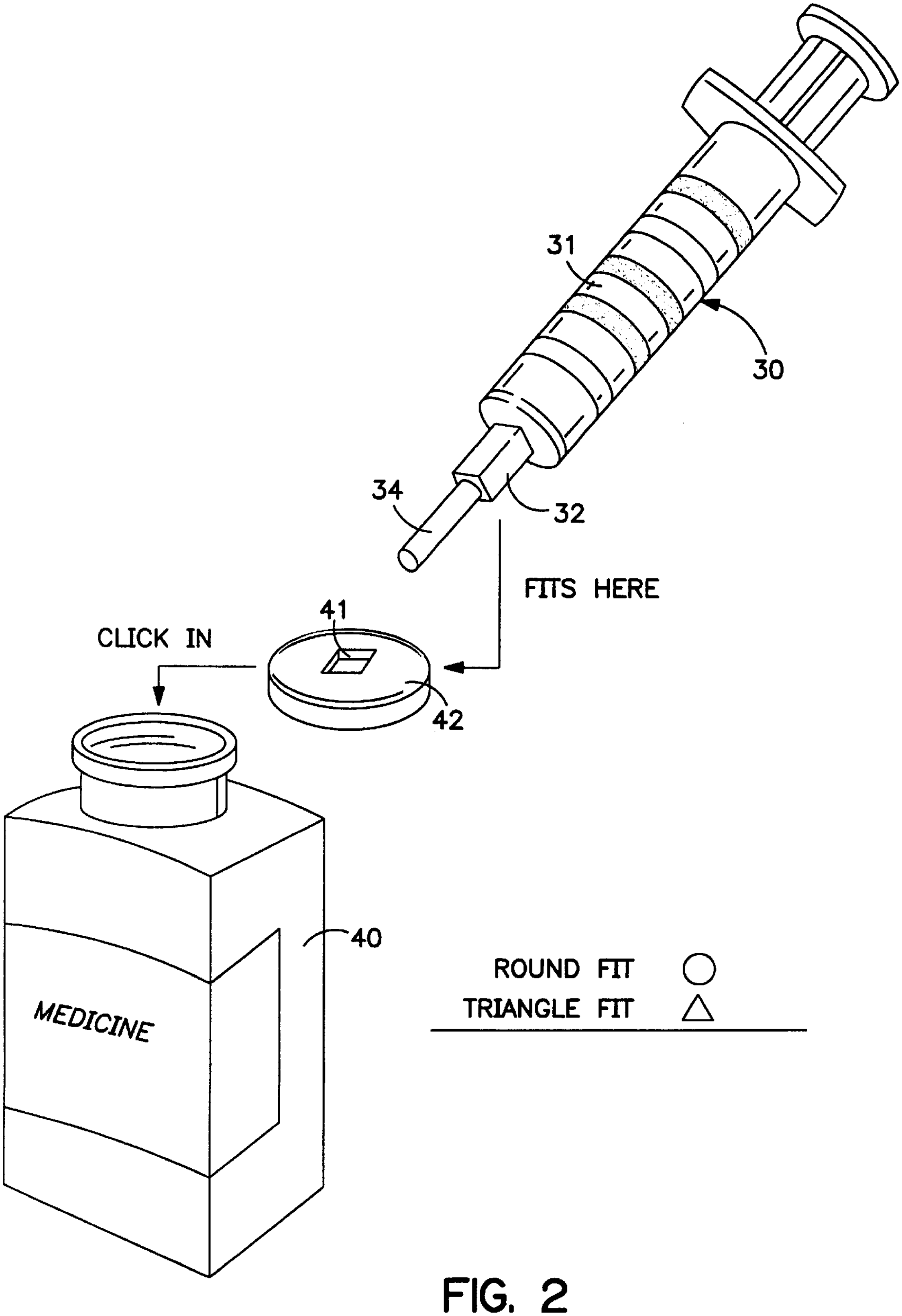
FIG. 2 is another embodiment of the invention which uses a mating syringe and dispensing bottle.

Referring now to FIG. 2, a further refinement on the invention is disclosed. This embodiment may be more suitable for use by parents, guardians or daycare employees for dispensing OTC medications such as cough syrup or oral prescription medications. A syringe 30 includes a reservoir 31 marked with dosage gradations in a set order of colors, as described above. Syringe 30 also includes a barrel 32 which communicates with the reservoir 31 and receives a hollow needle or tube 34 through which the medication is syphoned from a bottle 40. Barrel 32 has a square cross-section and matingly fits into a like-sized square orifice 41 in an inner bottle cap 42. Different concentrations of medication would be packaged in bottles with an inner cap having, for example, a triangular, round or hexagonal orifice. Various structural details are within the scope of the invention. For example, the barrel 32 may be designed in such a way as to not permit the medication in the bottle to be syphoned if the syringe 30 is inserted into a bottle with a mismatched inner cap 42.

Figure 3:
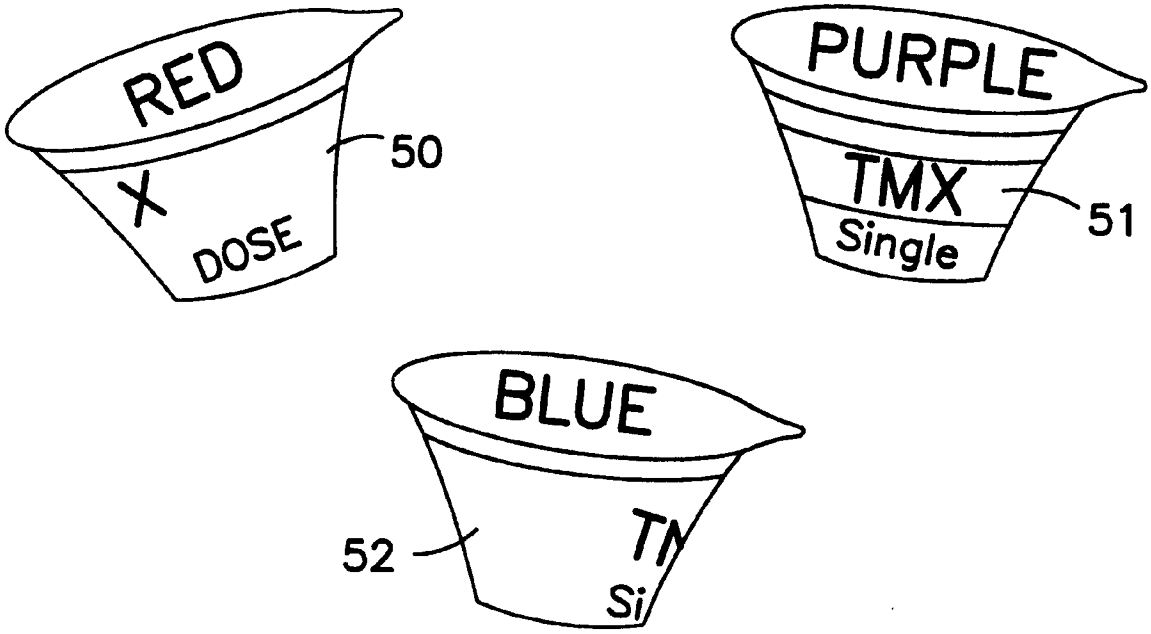
FIG. 3 is an illustration of a dosing system for single dose antibiotic powder for reconstitution and oral use.

As is shown in FIG. 3, single doses of various powders can be packaged in small plastic cups 50, 51 and 52. The cups 50, 51 and 52 are color-coded so that all the person administering the drug need to is take one of the cups having a color corresponding to the color assigned to the patient, remove the lid and reconstitute the drug by adding the appropriate amount of water.

Figure 4:
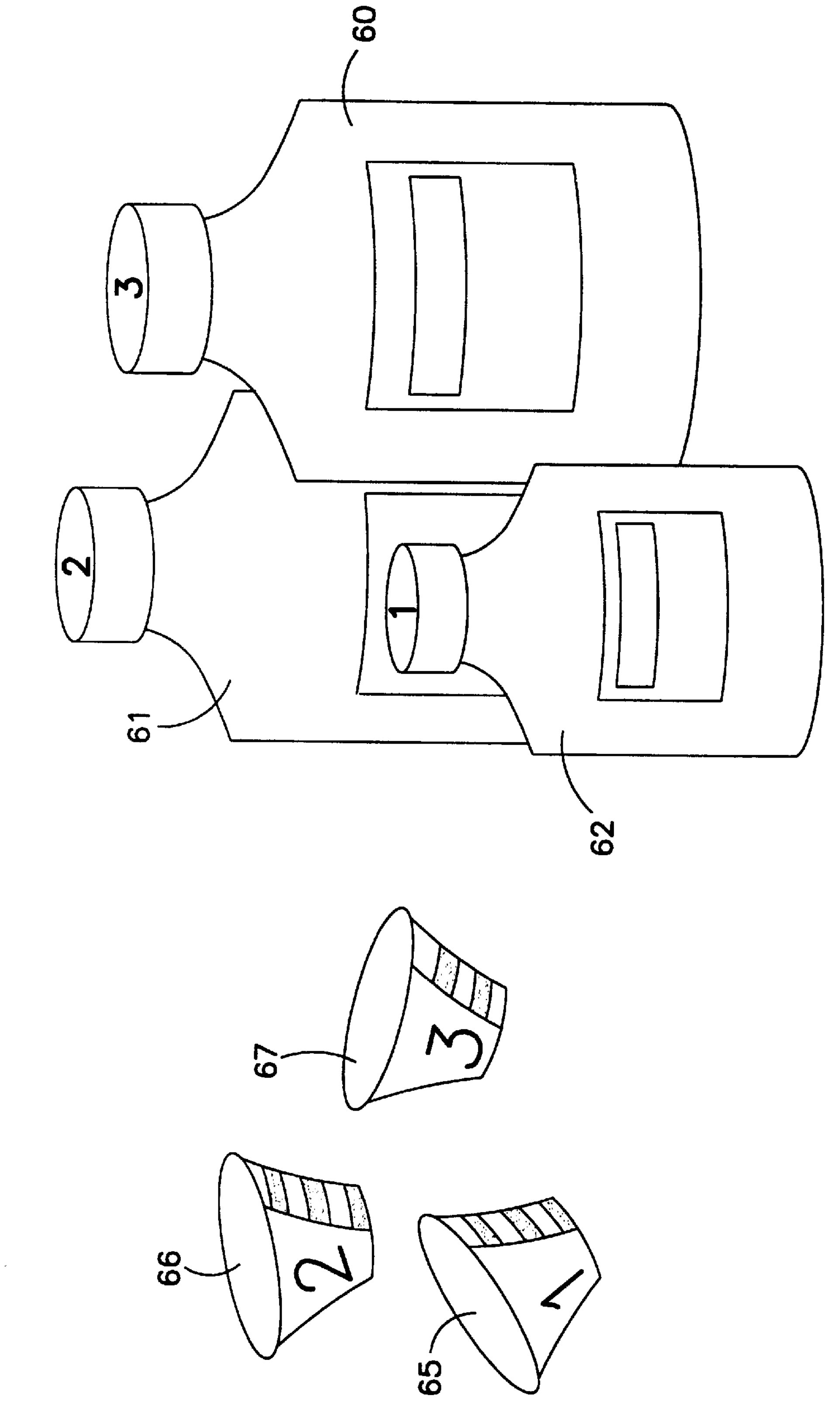
FIG. 4 is an illustration of a dosing system for over-the-counter (OTC) oral medications.

A similar procedure is shown in FIG. 4. Bottles 60, 61 and 62, identified with some markings such as numbers “1”, “2” and “3” are used with corresponding OTC dosage cups 65, 66 and 67. The cups 65, 66 and 67 have color-marked dosage gradations thereon which permit the proper amount of the medication to be dispensed from, for example, bottle 60 into cup 67. As described above with relation to FIG. 1, bottles 60, 61 and 62 contain differing concentrations of medication so that dispensing is correlated to the single color assigned to the patient.

A universal medication dosing system designed to aid in the practice of pediatric medicine is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. A method of determining the proper medication dosage for a patient, comprising the steps of:

(a) correlating a plurality of dosages of a plurality of medications to respective weight-related values indicative of the proper dosage of each of the medications for a given patient weight range;

(b) assigning a color to each of the respective weight-related values within a predetermined, fixed sequence of colors collectively representing a dosage range for each of the medications, wherein each of said colors represents a proper dosage for each medication for a patient having a weight within the weight range to which the color is assigned; and (c) providing a dosing system which correlates each of the dosages of said medications with the assigned color within the fixed sequence of colors.

2. A method of dosing a patient according to claim 1, wherein medications are correlated with the assigned color within the fixed sequence of colors without regard to the potency of said medication.

3. A method of dosing a patient according to claim 2, wherein said method includes the step of:

(a) prescribing a medication dosage of any of the plurality of medications by assigning a single color within the fixed sequence of colors to a patient based on the weight range of the patient which provides a proper dosage amount for each of the plurality of medications.

4. A method of dosing a patient according to claim 2, wherein said method includes the steps of:

(a) providing a medication container for a liquid medication having a medication-dispensing orifice with a predetermined-shape unique to the type and strength of the medication;

(b) providing a dosing syringe having a elongate medication-receiving barrel for dispensing medication from the medication container, said barrel having a size and shape adapted for being matingly-received in the medication container orifice for dispensing medication from the medication container; and (c) prescribing a dosage of the medication by assigning a single color to a patient based on the weight range of the patient which provides a proper dosage amount for each of the plurality of medications.

5. A method of determining the proper medication dosage for a patient, comprising the steps of:

(a) correlating a plurality of dosages to respective weight-related values indicative of the proper dosage of the medications for a given patient weight range; and (b) assigning a color to each of the respective weight-related values within a predetermined, fixed sequence of colors collectively representing a dosage range for the medication, wherein each of said colors represents a proper dosage for the medication for a patient having a weight within the weight range to which the color is assigned.

6. A method of dosing a patient according to claim 5, wherein said method includes the step of:

(a) prescribing a medication dosage by assigning a single color within the fixed sequence of colors to a patient based on the weight range of the patient which provides a proper dosage amount for each of the plurality of medications.

7. A method of dosing a patient according to claim 5, wherein said method includes the steps of:

(a) providing a medication container for a liquid medication having a medication-dispensing orifice with a predetermined-shape unique to the type and strength of the medication;

(b) providing a dosing syringe having a elongate medication-receiving barrel for dispensing medication from the medication container, said barrel having a size and shape adapted for being matingly-received in the medication container orifice for dispensing medication from the medication container; and (c) prescribing a dosage of the medication by assigning a single color to a patient based on the weight range of the patient which provides a proper dosage amount for the medication.

8. A method of determining the proper medication dosage for a patient, comprising the steps of:

(a) correlating a plurality of dosages of a medication to respective values indicative of the proper dosage of each of the medications for a given patient, wherein said values represent a direct correlation between a predetermined weight range of a patient and the dosage;

(b) assigning a color to each of the respective values within a predetermined, fixed sequence of colors collectively representing a dosage range for the medication, wherein each of said colors represents a proper dosage for the medication for a patient having a weight within the weight range to which the color is assigned.

9. A method of dosing a patient according to claim 8, wherein said method includes the step of:

(a) prescribing a medication dosage of the medication by assigning a single color within the fixed sequence of colors to a patient based on the weight range of the patient which provides a proper dosage amount for the medication.

10. A method of dosing a patient according to claim 9, wherein said method includes the step of:

(a) prescribing a medication dosage of any of the plurality of medications by assigning a single color within the fixed sequence of colors to a patient based on the weight range of the patient which provides a proper dosage amount for each of the plurality of medications.

11. A method of dosing a patient according to claim 10, wherein said method includes the steps of:

(a) providing a medication container for a liquid medication having a medication-dispensing orifice with a predetermined-shape unique to the type and strength of the medication;

(b) providing a dosing syringe having a elongate medication-receiving barrel for dispensing medication from the medication container, said barrel having a size and shape adapted for being matingly-received in the medication container orifice for dispensing medication from the medication container; and (c) prescribing a dosage of the medication by assigning a single color to a patient based on the weight range of the patient which provides a proper dosage amount for each of the plurality of medications.

* * * * *